United States Patent [19]

Jones

[11] Patent Number: 4,706,672
[45] Date of Patent: Nov. 17, 1987

[54] THERAPEUTIC THERMAL TRANSFER DEVICE

[76] Inventor: Robert C. Jones, 8427 Grand Ave., Duluth, Minn. 55808

[21] Appl. No.: 789,300

[22] Filed: Oct. 15, 1985

Related U.S. Application Data

[63] Continuation-in-part of Ser. No. 536,366, Sep. 26, 1983, abandoned.

[51] Int. Cl.$^4$ .............................................. A61F 7/00
[52] U.S. Cl. .................................. 128/379; 62/259.3; 128/402; 165/46
[58] Field of Search ...................... 128/379, 402, 156; 2/2.5, DIG. 1; 62/259.3; 165/46

[56] References Cited

U.S. PATENT DOCUMENTS

| | | | |
|---|---|---|---|
| 3,425,487 | 2/1969 | Tucker | 62/530 X |
| 3,491,761 | 1/1970 | Baker | 128/402 |
| 3,596,657 | 8/1971 | Eidus | 128/156 |
| 3,861,389 | 1/1975 | Winther | 128/403 X |
| 3,889,684 | 6/1975 | Lebold | 128/403 X |
| 4,126,903 | 11/1978 | Horton | 2/DIG. 1 X |

FOREIGN PATENT DOCUMENTS

| | | | |
|---|---|---|---|
| WO82/02148 | 7/1982 | PCT Int'l Appl. | 128/1 R |
| 252032 | 5/1926 | United Kingdom | 128/383 |
| 399092 | 9/1933 | United Kingdom | 128/379 |

Primary Examiner—Anton O. Oechsle
Attorney, Agent, or Firm—Douglas L. Tschida

[57] ABSTRACT

A therapeutic passive thermal transfer device for persons afflicted by disease, injury and the many forms of arthritis. The device is constructed of a plurality of metallic fibers woven into a porous screenlike mesh which allows for skin contact and air circulation thereover and through. Attachment means secure the device to a desired body part and allow the absorption of body heat from the afflicted body part and the transfer therefrom to the ambient air, with normal air circulation thereover. A thermally non-insulating cloth cover absorbs moisture and permits evaporation.

4 Claims, 4 Drawing Figures

THERAPEUTIC THERMAL TRANSFER DEVICE

RELATED U.S. APPLICATION DATA

Continuation-in-Part of Ser. No. 536,366, filed 09/26/83, abandoned.

BACKGROUND OF THE INVENTION

This invention deals with the therapeutic treatment of persons afflicted with various diseases and injuries and, more particularly, with the many forms of arthritis and the localized transfer of heat from the afflicted areas.

Cold pack devices have historically been employed in the treatment of patients suffering from fever and other diseases that induce relatively high body temperatures and which, depending on the ailment, is oftentimes localized to particular areas of the body. While the construction of such devices can take many forms, they are all intended to actively cool the patient by applying an artificially cooled medium to the afflicted area. A sufficiently large temperature gradient is thereby established and which induces thermal transfer and the cooling of the underlying tissue to offset the internally generated body heat. Such devices also commonly employ a pliant sealable envelope for containing ice or other refrigerable medium and for conforming to the afflicted area.

Similarly, heat pack devices have been used to transfer heat to reduce stiffness and similar ailments. In contrast to the cold packs, though, such devices typically rely on a contained heating element. A thermal insulator or temperature control prevents burning the user. The object however is again to actively promote a large temperature gradient and transfer heat to the body.

In contrast to either of the foregoing device types, the present invention contemplates a device for promoting the transfer of heat from the body as by a so-called heat sink. That is, it contemplates a passive, in the sense of not relying on an external heat or cold source, interface device or heat exchanger which absorbs heat from the patient and transfers the heat to the ambient air upon passing air over the surface of the heat sink.

SUMMARY OF THE INVENTION

The present "heat sink" device is constructed of a plurality of metallic fibers which are woven into a screenlike mesh that is intended for mounting over the skin of a patient in proximity to a heat producing body area. It contains no external connection to any energy source, and acts to passively absorb and transfer the body heat to the ambient air.

In application, the device is placed in thermally conductive proximity to the patient's skin and due to its superior thermal conduction properties, relative to the skin, absorbs the body heat. Ambient air circulating around and through the pores of the mesh exchange the heat to the air and thereby passively cool the patient. The pliability of the mesh permits it to conform to the intended body surface and fastener means secure it thereto.

In various embodiments, the woven mesh is mounted in relation to a thermally non-insulating cloth cover of one or more layers. The cloth covering is porous and allows air to circulate in and around the mesh and underlying skin and moisture to evaporate therefrom. Tie straps attached to the multi-layered assembly secure the assembly to the afflicted body part with the mesh in thermal transfer relation to the skin, and in a fashion that permits patient mobility. The multi-layer assembly may also be constructed in various shapes and sizes to accommodate particular body parts, such as the wrist, elbow, shoulder, back or leg etc.

It is therefore a primary object of the invention to provide comfort and mobility, with an inexpensive heat sink device that is safe to wear, simple to use, and allows passive cooling of the body. These and other advantages as well as the construction of the invention in various of its embodiments will however become more apparent upon directing attention to the following description thereof and the appended drawings and wherein like reference numerals refer to the same or similar parts.

DESCRIPTION OF THE PREFERRED EMBODIMENT

Figure 1:
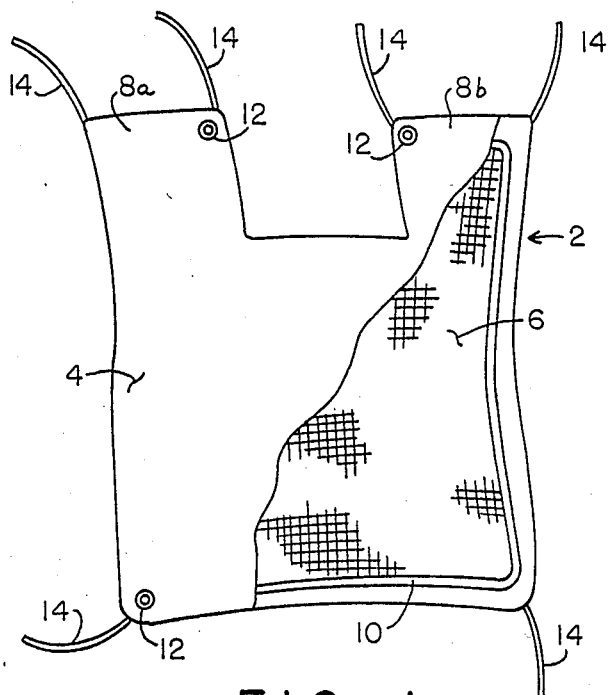
FIG. 1 shows in partial cutaway a front elevation view of the invention.

Referring to FIG. 1, the present thermal transfer device 2 is shown in a partially cutaway front elevation view. As depicted, the device 2 is constructed in a multi-layer mat-like configuration. Specifically, it is comprised of a porous envelope 4 in the center of which is contained a brass mesh 6. Depending then upon the area of the body for which the device 2 is intended, the cloth covering 4 and mesh 6 can be cut to an appropriate shape before assembly so as to permit a close fitting mounting of the assembly 2 in relation thereto and good contact with the skin.

As depicted in FIG. 1, the assembly 2 generally comprises a rectangular structure, approximately 24 inches tall by 12 inches wide. A cutout region is provided at the top-center of the assembly, and whereby a pair of elongated end portions 8a and 8b are obtained and the uses of which will become more apparent hereinafter. It is to be appreciated though that depending upon the intended body part, the shape of the assembly 2 can be cut as desired.

Turning attention to the mesh 6, upon cutting it to a desired shape, the edges are wrapped with a tape or other suitable edge covering 10 to prevent the unraveling of the mesh and possible injury to the user, should the unraveled ends project through the cloth envelope 4. Where however a selvage edge is provided in the material, the tape 10 may be deleted. While too a brass mesh is presently used, having individual pore sizes of approximately 1/16th by 1/16th inch, it is to be appreciated that various other conductive metal meshes may be used of smaller or larger mesh spacings. So too can different fiber materials, such as brass and copper or copper and zinc, be used at the same time and which upon the application of heat thereto act to produce a thermocouple effect which for some unexplained reason appears to enhance the properties of the present invention. The primary concern however for the selection of any one conductor over another being that it be biocompatible and not induce any undesired reactions with the skin, yet provide good thermal transfer properties.

It is also a belief of this inventor that the conductors be of a material similar to that found in the body.

Turning attention next to the cloth covering 4, it generally is constructed with all of its edges sewn closed or sealed, except one and which allows the insertion and/or removal of the mesh 6 thereat. In FIG. 1, the open edge is provided along the bottom of the assembly 2 and a number of snap fasteners 12 are provided therealong to removably secure the mesh 6 therein. Thus, the mesh 6 can be periodically removed to permit cleaning the covering 4.

Also mounted to each of the corners of the assembly 2 are cloth straps or ties 14 and which upon mounting the assembly 2 to an appropriate body part may be tied to secure the assembly 2 thereto. Also, it is to be appreciated that mating ones of the fasteners 12 can be disposed about the surface of the cloth covering 4 to further facilitate the wrapped attachment of the assembly 2 to the body part. For example, the assembly 2 of FIG. 1 includes a pair of mating snap fasteners 12 at the elongated side portions 8a and 8b. Alternatively, Velcro½ strips, hook and eye fasteners, buttons or the like can be provided in addition to or in lieu of the tie straps 14.

While too the embodiment of FIG. 1 contemplates the use of a thermally non-insulating cloth covering 4 in relation to the mesh 6, in some circumstances, such a covering 4 can alternatively be deleted or be mounted on only one side of the mesh 6. In this way, the mesh 6 can be brought into direct contact with the skin over a greater surface area and provide better heat transfer. By using the cloth covering 4, however, undesired chemical reactions between the skin and mesh 6 are minimized. Also, the mesh 6 is isolated from overlying clothing and which might too be stained and/or otherwise affected by the mesh 6 and/or perspiration. Where too a patient might be susceptible to an allergic reaction with the mesh 6, a cloth covering 4 is of particular advantage.

It is also to be appreciated that the porosity of the fabric covering 4, like that of the mesh 6, can be adjusted as desired to provide a suitable mounting relation to the patient's skin. The material of the covering 4 may also be varied as desired. In the presently preferred embodiment cotton is used, due to the ease of sewing and cleaning, although other materials could be substituted therefore. For example, a nylon mesh, such as used in women's stockings could be used and which also reduces the thickness of the cloth interface between the mesh 6 and lower lying skin. Any such material, however, should be as thermally transmissive as possible, and not a thermal insulator.

Figure 2:
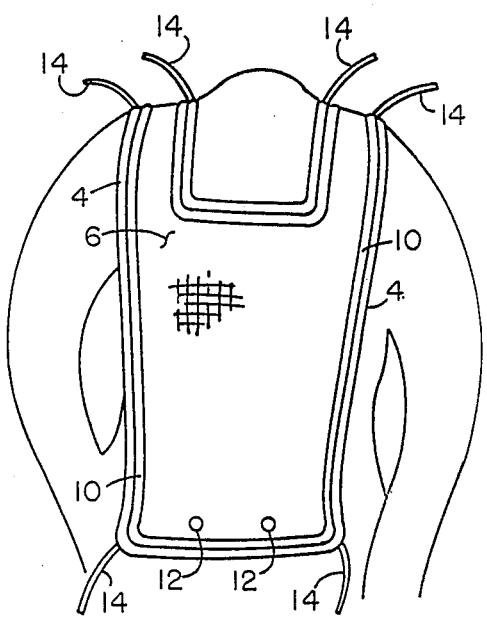
FIG. 2 shows an elevational view of the invention positioned over a patient's upper back and shoulders.
Figure 3:
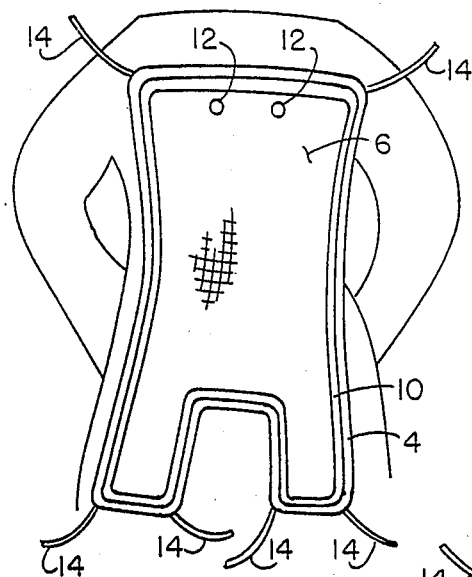
FIG. 3 shows an elevational view of the invention positioned over the lower back and hips.
Figure 4:
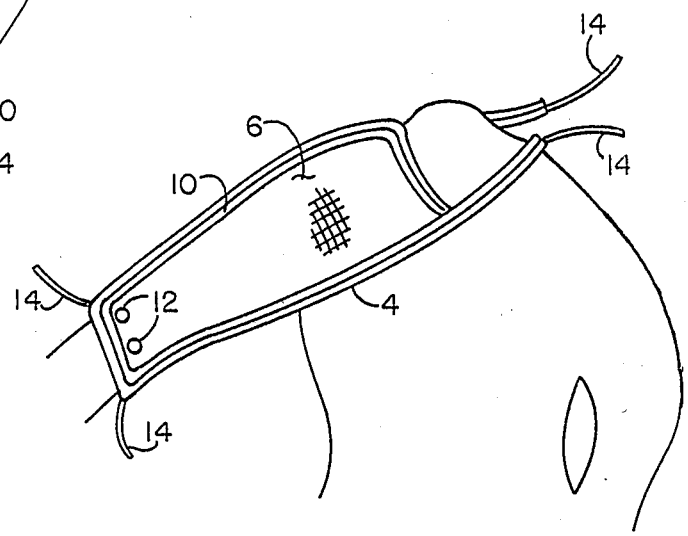
FIG. 4 shows an elevational view of the invention positioned over the arm and shoulder.

Turning attention next to FIGS. 2 through 4, various alternative mountings are shown of the assembly 2 relative to a user's anatomy. Specifically, FIG. 2 shows an elevation view of the assembly 2 in mounted relation to the back, chest and abdominal area of the user. In this position, the ends 8a and 8b are secured about the shoulders with the upper tie straps 14, while the lower tie straps 14, secure the assembly about the waist 2. As depicted, too, a single layer of cloth 4 between the skin and mesh 6 is used, instead of two layers. It is to be appreciated too that alternatively the mesh 6 could be placed adjacent the skin in lieu of the cloth 4.

FIG. 3 shows an elevation view of the assembly 2 of FIG. 2 in mounted relation to the back of a user. Here however the elongated portions 8a and 8b are mounted over the buttocks and thighs, in lieu of about the shoulders. The attachment of the assembly 2 to the user's body, like that for FIG. 2, is achieved via the tie straps 14 and which may be tied to one another or to themselves, upon mounting the assembly 2 and depending upon the shape of the desired body part.

Directing attention lastly to FIG. 4, a view is shown of the assembly 2 in mounted relation about the patient's arm, particularly the elbow and shoulder area. For this mounting, upon wrapping the assembly 2 about the arm, the upper end is secured by tying the straps 14 about the patient's neck. The lower end, in turn, is secured about the arm at the portions 8a and 8b via the mating fasteners 12 attached thereto, as well as with the ties 14. As mentioned previously, still other fasteners might be included along the edges or on the surfaces of the covering 4 such that upon wrapping the assembly 2 about the body part, the fasteners will overlie one another.

While the present invention has been described with respect to its presently preferred embodiment and various presently contemplated alternative embodiments, it is to be appreciated that in addition to the foregoing modifications, still others may suggest themselves to those of skill in the art. Accordingly, it is contemplated that the following claims should be interpreted so as to include all those equivalent embodiments within the spirit and scope thereof.

What is claimed is:

1. A heat transfer garment comprising:
   (a) an air permeable metallic meshwork constructed of a plurality of woven metal fibers, wherein ones of said fibers are of a first metal and others are of a second different type metal, wherein the peripheral edges of said meshwork are bound to prevent fraying and wherein said meshwork is of a generally rectangular shape and includes first and second spaced apart elongated portions extending outwardly from one edge thereof;
   (b) an air permeable, thermally transmissive cloth envelope for removably containing said meshwork, said meshwork mounting therein at a resealable opening, and having a plurality of tie straps secured about the periphery thereof; and
   (c) a plurality of mating fasteners secured about the surface of said cloth envelope whereby said tie straps and fasteners cooperatively secure said meshwork in thermal transfer relation to selected body parts.

2. Apparatus as set forth in claim 1 wherein said first metal fibers are zinc and said other second metal fibers are copper.

3. Apparatus as set forth in claim 1 wherein the surface of said cloth covering in contact with the wearer's skin is made of nylon.

4. Apparatus as set forth in claim 1 wherein said cloth covering comprises an envelope having a resealable opening and at least one surface of a nylon material.

* * * * *